United States Patent
Barna et al.

(10) Patent No.: US 12,075,543 B2
(45) Date of Patent: Aug. 27, 2024

(54) CIRCADIAN STIMULUS ILLUMINATION CONTROL SYSTEMS AND METHODS

(71) Applicant: RAB Lighting Inc., New York, NY (US)

(72) Inventors: Ross A. Barna, New York, NY (US); Jason Lawrence Oliver, Rye, NY (US)

(73) Assignee: RAB Lighting Inc., New York, NY (US)

( * ) Notice: Subject to any disclaimer, the term of this patent is extended or adjusted under 35 U.S.C. 154(b) by 82 days.

(21) Appl. No.: 17/080,819

(22) Filed: Oct. 26, 2020

(65) Prior Publication Data
US 2021/0045220 A1 Feb. 11, 2021

Related U.S. Application Data

(63) Continuation-in-part of application No. 16/402,385, filed on May 3, 2019, now Pat. No. 10,820,396.
(Continued)

(51) Int. Cl.
*H05B 47/155* (2020.01)
*A61M 21/00* (2006.01)
(Continued)

(52) U.S. Cl.
CPC .......... *H05B 47/155* (2020.01); *A61M 21/00* (2013.01); *H05B 45/10* (2020.01); *H05B 45/20* (2020.01);
(Continued)

(58) Field of Classification Search
CPC .......... A61M 21/00; A61M 2021/0044; A61M 2205/3306; A61M 2205/3553;
(Continued)

(56) References Cited

U.S. PATENT DOCUMENTS

| 5,905,442 A | 5/1999 | Mosebrook |
|---|---|---|
| 9,220,202 B2 | 12/2015 | Maxik et al. |

(Continued)

FOREIGN PATENT DOCUMENTS

| WO | WO-2018093803 A1 * | 5/2018 | ............ H05B 45/10 |

OTHER PUBLICATIONS

Mika Raatikainen, Robert Ciszek, Johanna Narvainen, Juho Merilahthi, Sami Siikanen, Timo Ollikainen, Ilona Hallikainen, Jukka-Pekka Skon; System Architecture of Customized Intelligent Lighting Control and Indoor Environment Monitoring System for Persons with Mild Cognitive Impairment or Dementia; published Sep. 14-16, 2016; retrieved from <http://ieeexplore.ieee.org/abstract/document/7749463/>.

(Continued)

*Primary Examiner* — Raymond R Chai
(74) *Attorney, Agent, or Firm* — Innovation Law Office; Dennis S. Schell

(57) ABSTRACT

Circadian stimulus illumination control systems and methods are disclosed. Embodiments include a control system providing selection of a preset circadian stimulus profile, including a desired circadian stimulus level for setpoint times, for example, including a color temperature and brightness level for each setpoint time to simulate local natural sunlight conditions or a different selected lighting and/or stimulus condition. The control system wirelessly transmits information for the setpoints of the profile to lighting devices, which incrementally transition the color temperature and dimming of the lighting device between the profile setpoints.

20 Claims, 7 Drawing Sheets

Related U.S. Application Data

(60) Provisional application No. 62/666,410, filed on May 3, 2018.

(51) Int. Cl.
   *H05B 45/10* (2020.01)
   *H05B 45/20* (2020.01)
   *H05B 47/16* (2020.01)
   *H05B 47/19* (2020.01)

(52) U.S. Cl.
   CPC ............. *H05B 47/16* (2020.01); *H05B 47/19* (2020.01); *A61M 2021/0044* (2013.01)

(58) Field of Classification Search
   CPC ...... A61M 2205/3584; A61M 2205/84; A61M 2230/63; A61N 5/0618; A61N 2005/0628; H05B 45/10; H05B 45/20; H05B 47/155; H05B 47/16; H05B 47/19; Y02B 20/40
   See application file for complete search history.

(56) References Cited

U.S. PATENT DOCUMENTS

| | | | |
|---|---|---|---|
| 9,636,520 B2 | 5/2017 | Pedersen | |
| 2007/0273307 A1* | 11/2007 | Westrick | H05B 47/16 315/312 |
| 2011/0221348 A1* | 9/2011 | Kwag | H05B 47/19 315/130 |
| 2012/0319819 A1 | 12/2012 | Tkachenko | |
| 2013/0076491 A1 | 3/2013 | Brandsma et al. | |
| 2014/0070707 A1* | 3/2014 | Nagazoe | H04B 10/116 315/151 |
| 2016/0073483 A1 | 3/2016 | Setomoto et al. | |
| 2016/0212694 A1 | 7/2016 | Lindoff et al. | |
| 2016/0295658 A1* | 10/2016 | Chraibi | F21V 19/006 |
| 2017/0105265 A1 | 4/2017 | Sadwick | |
| 2017/0189640 A1 | 7/2017 | Sadwick | |
| 2017/0238401 A1 | 8/2017 | Sadwick et al. | |
| 2017/0245354 A1* | 8/2017 | Yadav | H05B 47/19 |
| 2018/0153024 A1 | 5/2018 | Hadachi | |
| 2018/0235062 A1* | 8/2018 | Kurihara | H05B 45/10 |
| 2019/0150250 A1* | 5/2019 | Hatano | H04B 10/11 315/130 |
| 2019/0297704 A1 | 9/2019 | van de Ven | |
| 2020/0037146 A1* | 1/2020 | Salkintzis | H04W 12/06 |
| 2022/0159802 A1* | 5/2022 | Lang | H05B 45/20 |

OTHER PUBLICATIONS

Ali Motamed, Marta Benedetti, Jean-Louis Scartezzini; On the Impart of Integration of Non-Image Forming (NIF) Effect of Light on Electrical Lighting Control in Non-Residential Buildings; published in 2016; retrieved from <http://www.iaqvec2016.org/download/Files/1231.pdf>.

Dr. Mark Rea, Aaron Smith, Andrew Bierman, Dr. Mariana Figuerio; The Potential of Outdoor Lighting for Stimulating the Human Circadian System; published on Apr. 9, 2014; retrieved from <http://www.ee.co.za/article/potential-outdoor-lighting-stimulating-human-circadian-system.html>.

* cited by examiner

CIRCADIAN STIMULUS ILLUMINATION
CONTROL SYSTEMS AND METHODS

PRIORITY

This application claims the benefit of and is a Continuation-in-Part application of U.S. Nonprovisional Application Ser. No. 16/402,385, filed May 3, 2019, and titled "Illumination Control Systems and Methods," which claims the benefit of U.S. Provisional Application No. 62/666,410, filed May 3, 2018, and titled "Illumination Control Systems and Methods," the entireties of which are hereby incorporated herein by reference.

TECHNICAL FIELD

Embodiments of this disclosure relate generally to control systems and more particularly to wireless lighting control systems for adjusting the color temperature and brightness level of a plurality of lighting devices.

BACKGROUND

Circadian rhythms are physical, mental, and behavioral changes in humans, plants, and animals that follow a roughly 24-hour cycle, responding primarily to light and darkness in the environment. Circadian rhythms can influence sleep-wake cycles, hormone release, body temperature and other important bodily functions. Research exists indicating that humans perform better and are healthier when indoor lighting is brightness level adjusted and color-corrected, sometimes referred to as "color tuning," or, more specifically, "white tuning," to represent the actual outdoor lighting conditions as provided by the sun for the specific time of day (e.g., warmer color and dimmer in the morning, cooler and brighter as the day transitions to midday, and warmer and dimmer again as the day transitions to afternoon and evening).

SUMMARY

To provide these desired lighting effects within an indoor environment, all indoor lighting devices would need to continually adjust and synchronize with one another throughout the day and night. This should hold true even when individual lighting devices are periodically powered on/off. Existing lighting devices achieve this by including atomic clocks and color-correction capabilities onboard each individual lighting fixture to ensure all fixtures color-correct immediately upon being turned on.

However, incorporating such technology into each lighting fixture can become expensive and cost-prohibitive for users commissioning a large number of lighting devices. It was realized by the inventors of the current disclosure that improvement in the existing circadian stimulus lighting adjustment technology is needed to allow continual, large-scale color temperature adjustments throughout the day. Further, it is important to do so in a low-cost manner. Embodiments of the present disclosure provide an improved illumination control system and method of using the same.

Circadian stimulus illumination control systems and methods are disclosed. Embodiments include a control system providing selection of a preset circadian stimulus profile, including desired a desired circadian stimulus level for setpoint times, for example, including a color temperature and brightness level for each setpoint time to simulate local natural daylight conditions or a different selected lighting and/or stimulus condition. The control system wirelessly transmits information for the setpoints of the profile to lighting devices, which incrementally transition the color temperature and dimming of the lighting device between the profile setpoints.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein does not necessarily address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions or may have been created from scaled drawings. However, such dimensions, or the relative scaling within a figure, are by way of example, and not to be construed as limiting.

DETAILED DESCRIPTION OF THE ILLUSTRATED EMBODIMENTS

Figure 1:
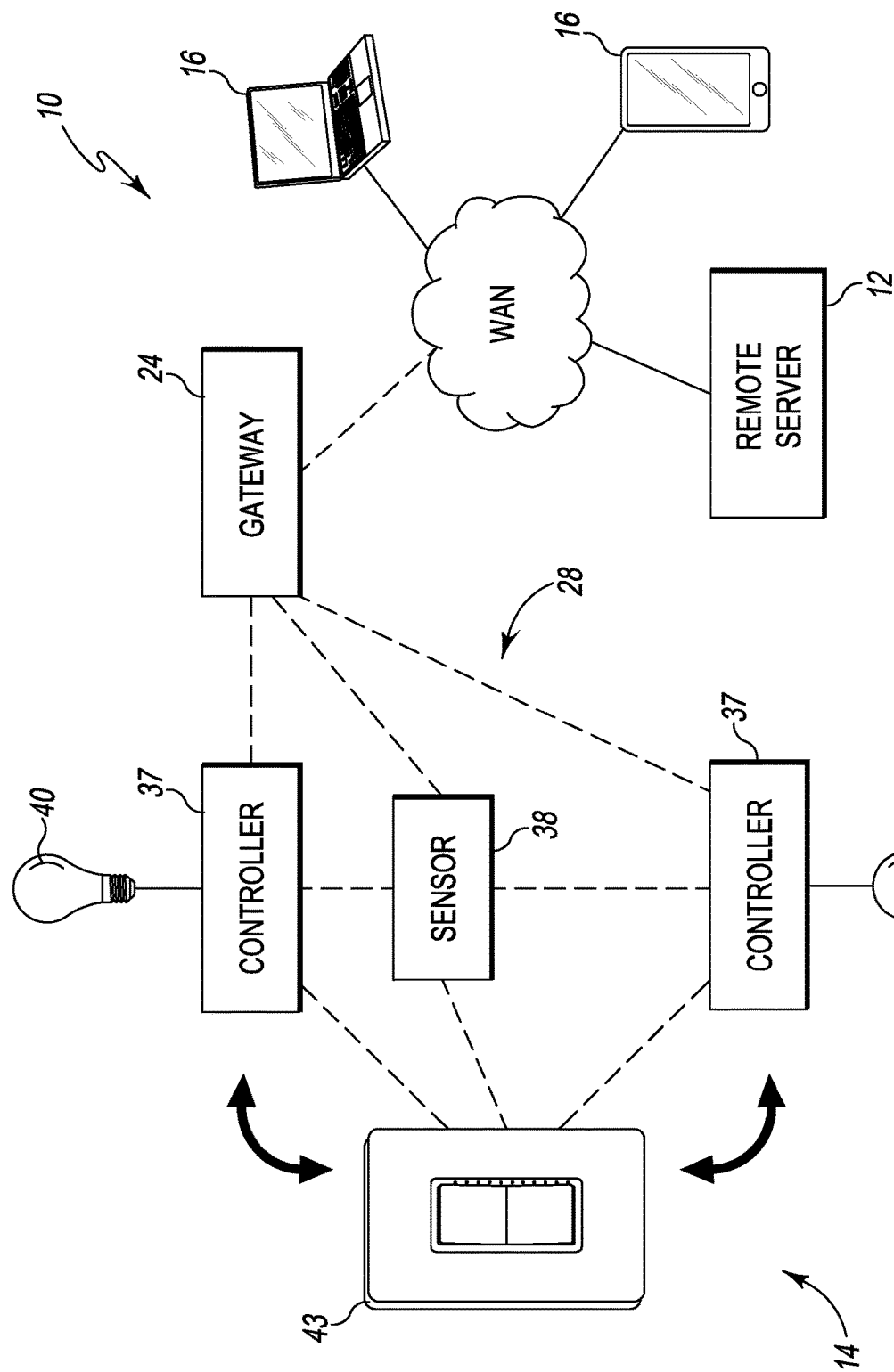
FIG. 1 illustrates an overview of a first exemplary illumination control system according to the present disclosure.

For the purposes of promoting an understanding of the principles of the disclosure, reference will now be made to one or more embodiments, which may or may not be illustrated in the drawings, and specific language will be used to describe the same. It will nevertheless be understood that no limitation of the scope of the disclosure is thereby intended; any alterations and further modifications of the described or illustrated embodiments, and any further applications of the principles of the disclosure as illustrated herein are contemplated as would normally occur to one skilled in the art to which the disclosure relates. At least one embodiment of the disclosure is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to benefits or advantages provided by some embodiments, other embodiments may not include those same benefits or advantages, or may include different benefits or advantages. Any benefits or advantages described herein are not to be construed as limiting to any of the claims.

Likewise, there may be discussion with regards to "objects" associated with some embodiments of the present invention, it is understood that yet other embodiments may not be associated with those same objects, or may include yet different objects. Any advantages, objects, or similar words used herein are not to be construed as limiting to any of the claims. The usage of words indicating preference, such as "preferably," refers to features and aspects that are present in at least one embodiment, but which are optional for some embodiments.

Specific quantities (spatial dimensions, wavelengths, frequencies, dimensionless parameters, etc.) may be used explicitly or implicitly herein, such specific quantities are presented as examples only and are approximate values unless otherwise indicated.

The embodiments of the present disclosure provide devices and methods which enable circadian stimulation control of a plurality of lighting devices, and more specifically, controlling brightness (dimming) and color temperature to assist regulation of a biological (circadian) rhythm, and to provide other desirable illumination effects for an environment. The wireless illumination control system will first be introduced, then methods and devices associated with providing circadian stimulus control will be further described.

Wireless Illumination Control System

FIG. 1 illustrates an overview of an exemplary circadian stimulus illumination control system 10, according to the present disclosure. The exemplary system 10 generally includes a remote server, or backend system 12, one or more site systems 14, and various clients, also referred to throughout as user computer devices 16, for example, a graphical user interface device such as a smart phone, tablet, or other touch screen device. The server system 12 may communicate with the site system 14 and the user computer devices 16 over a wide area network (WAN) such as Internet 20 or a cellular network 22, and/or via a local area network (LAN).

Each site system 14 may generally include at least one base station or gateway 24, lighting control devices 37, sensors 38, user control devices 43, and a mesh network 28, or other local wireless network, that facilitates communication among site system 14 and controls lighting devices 40, which may be lamps or light fixtures. The gateway 24 serves as the manager/coordinator for site system 14 and mesh network 28, and provides connectivity to server system 12.

The lighting control devices 37 may include an actuator providing dimming, CCT, and/or on/off control for light fixtures 40. Lighting control devices 37 may be partly or fully integrated with lighting devices 40. User control device 43, such as a touch-screen device or wall switch, keypad, or dimmer, may be associated with one or more control devices 37 or zones of control devices 37 and lighting devices 40 to provide user selection of a desired lighting effect, for example, on/off, dimming, scene selection, and selection, activation, and/or override of a circadian stimulus profile schedule. Sensors, for example, an occupancy sensor 38 or a daylight harvester, can be used to provide automations for the site system 14, including for example, a change to the lighting effect provided by the user control device 43 depending on the state of the sensor 38, including selection or override of a circadian stimulus profile schedule.

Figure 2:
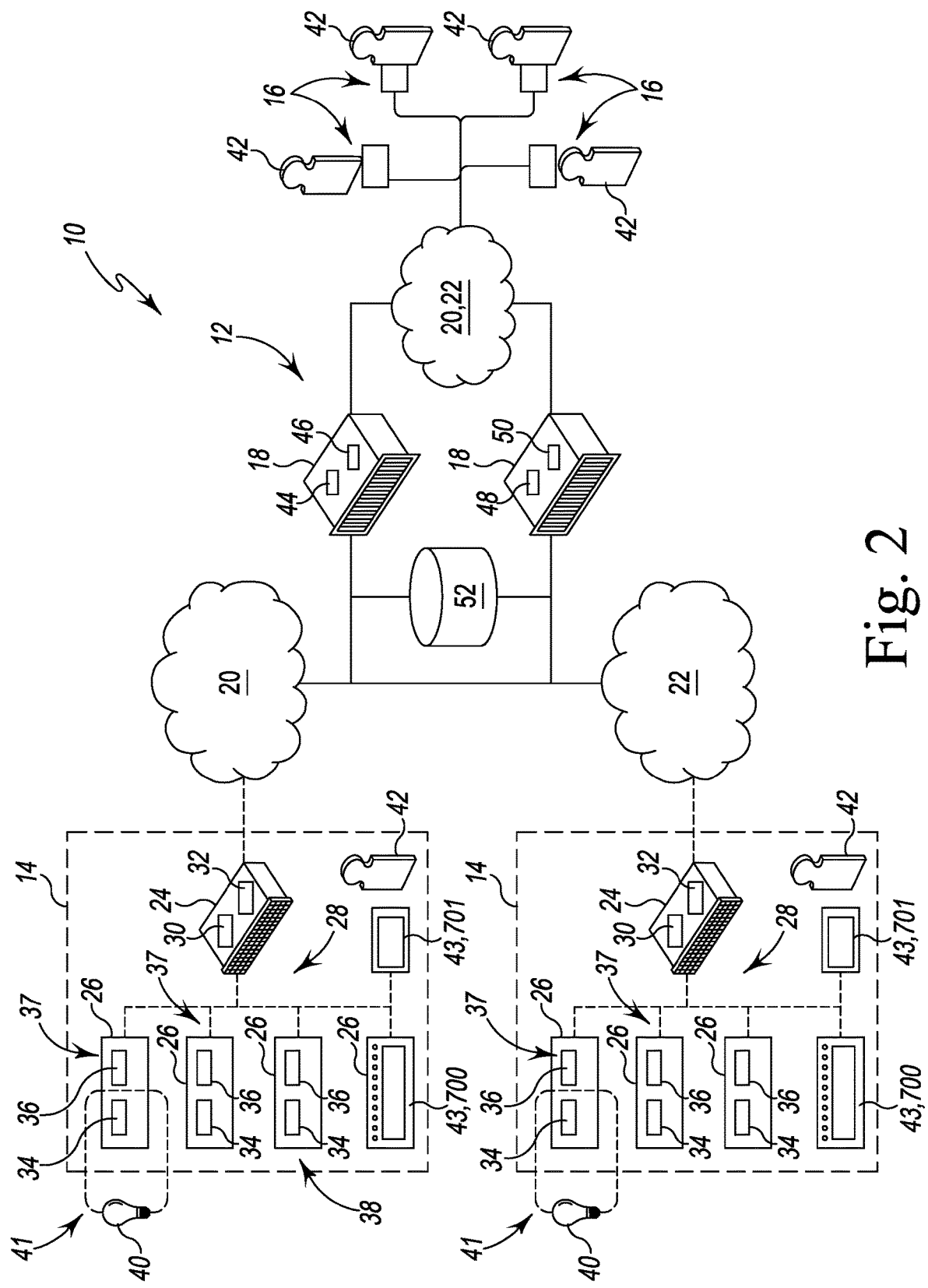
FIG. 2 illustrates the first exemplary illumination control system, according to the present disclosure.

FIG. 2 is a more detailed illustration of an exemplary circadian stimulus illumination control system 10, according to the present disclosure. Although a wireless lighting control system, for example the LIGHTCLOUD system available from RAB Lighting Inc. of Northvale, N.J., will be described, it should be appreciated that the systems and methods described herein are applicable to the automation, monitoring, and/or control of a variety of devices or components in a variety of environments. Exemplary site systems 14 may include all or portions, including indoor and/or outdoor portions, of a home, business, parking garage, street, worksite, or other location that include a predefined set of components, such as electrical devices or circuits, including, for example, lamps and light fixtures, to be monitored or controlled.

The server system 12 may include one or more servers, or computers 18 including typical computer components, such as a processor, memory, storage, display, network interface, and input/output device, for example. The processor, or processors, may execute unique sets of instructions, which may be implemented as computer readable program code, stored in memory or storage, such that the server system 12 is configured as a special purpose system. In particular, hardware, software, and particular sets of instructions may transform the server system 12, or portions thereof, into a lighting control server system, as described herein. As should be appreciated by those skilled in the art, the server system 12 may also include any combination of computer hardware and software that facilitates communication with the site systems 14 and user computer devices 16, and performance of the functions described herein.

According to a specific implementation, all or portions of the server system 12 may be cloud-based virtual servers, including a virtual private cloud-based service. That is, for example, the one or more servers 18 of the server system 12 may reside on the Internet, for example, rather than on a local computer. To be clear, the server system 12 may be remote from the site systems 14 and/or the user computer devices 16. The server system 12 may communicate with the site systems 14 and the user computer devices 16 over a wide area network (WAN), such as the Internet 20 or a cellular network 22, and/or via a local area network (LAN), for example. Some embodiments in particular use cellular communication.

Each site system 14 may generally include at least one site lighting controller, or gateway 24, and one or more wireless devices 26, or device nodes, which are configured to communicate over a mesh network 28, or other similar local wireless network.

The gateway 24 may include a communications module 30 that facilitates communication between the mesh network 28, or other wireless network, and the WAN network, such as the Internet 20 or a cellular network 22. As such, the gateway 24 can facilitate communication between the devices 26 of the site system 14 and the server system 12. The gateway 24 may also include an operations module 32 for processing and/or communicating instructions (e.g., to devices 26) received from the server system 12, as will be described in greater detail below. The operations module 32 may also receive, store in memory, and/or process information from the devices 26. That is, the gateway 24 may run applications locally while also interfacing across the mesh network 28 for WAN connectivity to the server system 12. An exemplary gateway device may be, for example, the LIGHTCLOUD Gateway available from RAB Lighting Inc. of Northvalle, N.J.

Each device 26 may include a communications module 34, facilitating communication between the device 26 and the gateway 24 over a local wireless network, such as the mesh network 28. For example, the devices 26 may each include a radio transceiver, such as a XBee® radio module for communicating using the ZigBee® protocol, which is related to IEEE standards, including 802.15.4. The devices 26 may also include at least one control module 36, including memory, for facilitating interaction between the device 26 and an associated electrical component, such as, for example, an electrical circuit. Devices 26 may also each be configured to act as a router or end device, such that it can also forward messages to other devices 26 and/or the gateway 24.

Each site 14 may include a variety of different devices 26 managed by the gateway 24 and connected to the mesh network 28. For example, according to one implementation, a site 14 may include lighting control devices 37, sensors, such as occupancy sensors, 38, daylight harvesters, and user control devices, such as touchscreens and wall dimmers, 43. In addition to controlling lighting devices 40, for example, lamps and light fixtures. Control devices 37 may be integral with, separate from, or partly integrated with lighting devices 40. Control device 37 may be configured to act an event trigger by detecting voltage and/or current to determine the state of a device, such as, for example, a room light switch or a light fixture having its own motion sensor, or other sensor, to activate it. Sensors 38 that are part of the system 10 may be configured to detect and report the state of motion sensors, for example occupancy/vacancy sensors, while daylight harvesters may include a light sensing circuit for measuring light and reporting measurements and other data to the system 10.

Each of the user computer devices, or clients, 16 may include a computing device, such as, for example, a touchscreen device, a personal computer, laptop computer, netbook computer, tablet device, mobile device, portable electronic device (PED), smart device, or cell phone configured to communicate with the server system 12 via WAN 20 or 22, or possibly with the gateway 24, for example, via mesh network 28, to permit a user 42 to configure, monitor, and/or control devices 26 for a particular site system 14, including using a graphical user interface to configure the circadian stimulus profile schedule.

The system 10 or, more specifically, the server system 12 may include a plurality of modules useful in carrying out the control and other strategies disclosed herein. For example, the server system 12 may include or utilize functionality expressed with reference to an organization account registration module 44, a user manager module 46, a device manager module 48, and a communications module 50, to name a few.

The wireless device control system 10 or, more specifically, the server system 12 may include a database management system including one or more databases, such as data repository 52. The data repository 52 may store data, including hardware and software configuration information for each site system 14, including information such as SPD, CCT, and dimming specifications and capabilities for each lighting device 40, and preset and configured circadian stimulus profile schedules associated with selected components of the site system 14. According to some embodiments, the data repository 52 may be initially populated with at least some default control data, including one or more circadian stimulus profile schedules.

Lighting Control Devices

As stated above, devices 26 of the wireless control system 10 and associated site lighting fixtures 40 may be controlled, monitored, and managed by users 42, via user computer devices 16 and user control devices 43. Generally speaking, devices 26 can act as actuators, causing changes in the environment (e.g., turning lights on or off, controlling CCT and dimming levels), user controls, detecting and responding to user interactions, and/or sensors, detecting and/or responding to some input from the environment, such as movement or light, at the respective sites. Although not an exhaustive list, some exemplary devices 26 are described further below and can include user control devices 43, occupancy/vacancy and other condition sensors 38, daylight harvesting sensors, and lighting control devices 37. In at least one embodiment, devices 26 can be LIGHTCLOUD Controllers with SMARTSHIFT or a lamp or light fixture integrated with a wireless controller, such as EZPAN SWISH light fixture with LIGHTCLOUD and SMARTSHIFT (EZPAN2X2/D10/SS/LC), available from RAB Lighting Inc. of Northvale N.J., or other tunable white lighting fixtures, for example, having subsets of LEDs comprising at least two different CCT levels that can be individually powered, i.e., dimmed, to provide a range of CCT levels and brightness levels.

User Control Devices

Referring to FIG. 1 exemplary user control devices 43, e.g. mechanical and touch-activated interfaces such as wall dimmer switches and touchscreens, reside at the site 14, for example, mounted to or recessed within a wall at a convenient location for the areas and zones controlled by the device. The user control device 43 may communicate directly with and control the devices 26 of the site system 14 via the mesh network 28, or communicate with the gateway 24. For example, lighting effects such as on/off or dimming control of one or more control devices 37 associated with a user control device 43 may utilize transmission of messages by device 43 addressed to specific control devices 37. Alternatively, lighting effects such as scene control may utilize transmission of a messages by device 43 addressed to the gateway 24 indicating the user interaction with device 43 and/or the desired scene, resulting in gateway 24 initiating control of appropriate control devices 37. As discussed further below for the first exemplary embodiment of the circadian stimulus illumination control system, the user control device 43 can be used to selectively override a circadian stimulus for a period of time.

The user control device 43 may include an integrated radio module, or may include an external radio module. If configuration or control of one or more devices 26 is affected from the user control device 43, the gateway 24 and ultimately the server system 12 and the user interface on a user computer device 16 may be updated accordingly with the new configuration and/or status of the devices 26, either by the user control device 43 or by the devices 26 themselves.

Figure 4:
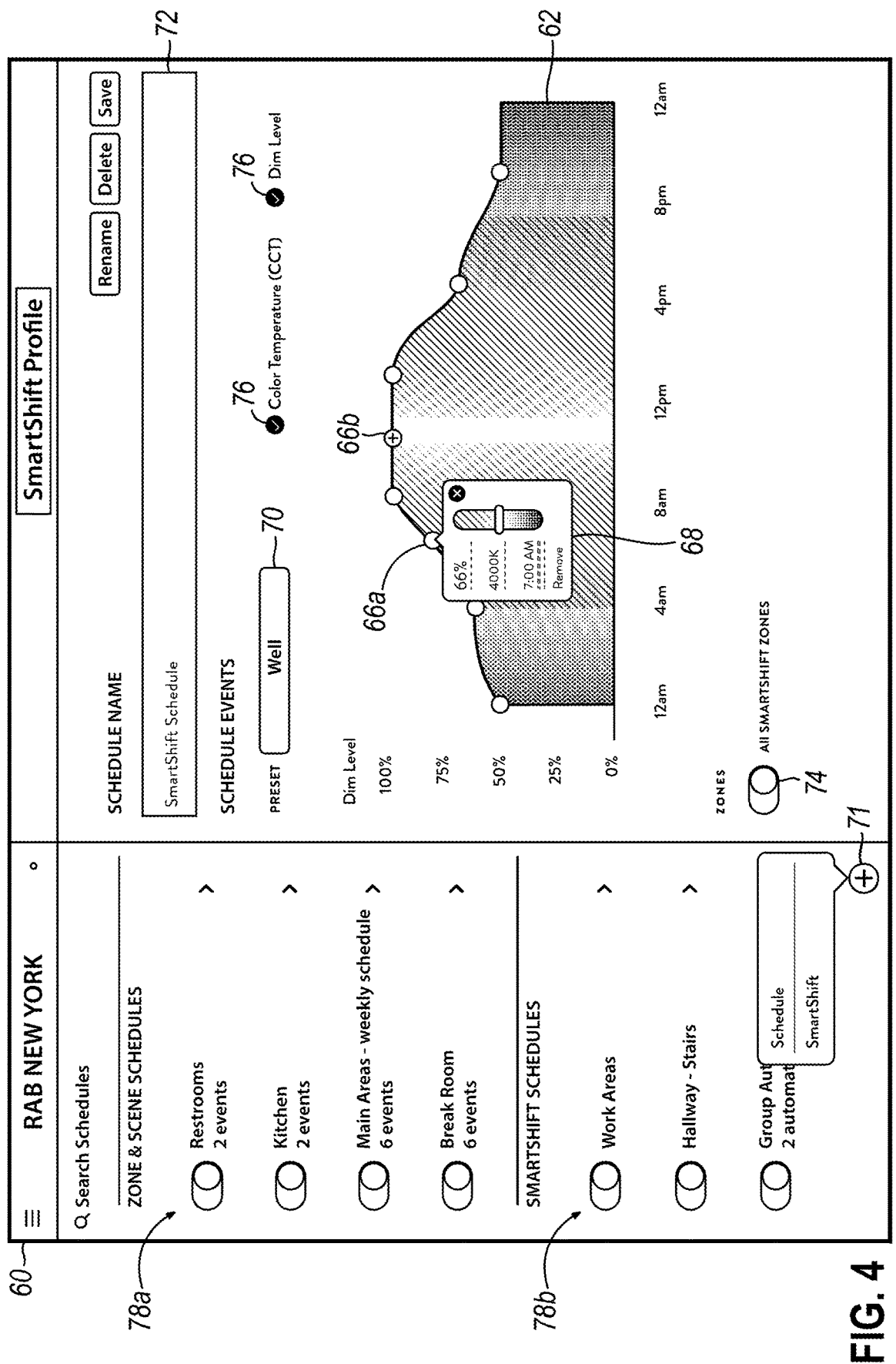
FIG. 4 illustrates a graphical user interface layout for the circadian stimulus control of the first exemplary illumination control system.

One embodiment of a user control device 43 is a touch-screen device, such as a tablet computing device, that functions like one of the user computer devices 16, having a graphical user interface application or software installed directly thereon, facilitating the system configuring, monitoring, and controlling as described herein, for example, the exemplary graphical user interface (GUI) planform as shown in FIG. 4 that provides configurable touch-activated user interface elements. For example, LIGHTCLOUD Touch or the LIGHTCLOUD smart device application, both available from RAB Lighting Inc. of Northvale, N.J.

An exemplary lighting control device 37, or lighting control device provides control of the lighting device 40 by using dimming and CCT control signals. The control device 37 may, thus, provide ON/OFF control, as well as dimming and CCT control for individual and/or integral lamps or light fixtures, or for lamps and light fixtures installed on the same circuit.

Gateway

At least one gateway, such as gateway 24 above, is installed to communicate with devices 26 at a site 14. With continued reference to the system 10 of FIG. 2, the gateway 24 serves as the coordinator of and manages the mesh network 28 and communicates with the server system 12. As will be described below, the gateway 24 ultimately controls the devices 26, with control information mirrored from the server system 12, with which users 42 and user computer devices 16 directly interact. According to at least one embodiment of the present disclosure, the gateway 24 communicates with the server system 12 via cellular or, in some particular embodiments, machine-to-machine cellular. Alternatively, a LIGHTCLOUD hub, available from RAB Lighting Inc. of Northvale, N.J., may be substituted for a gateway 24.

First Exemplary Circadian Stimulus Illumination System

Figure 3:
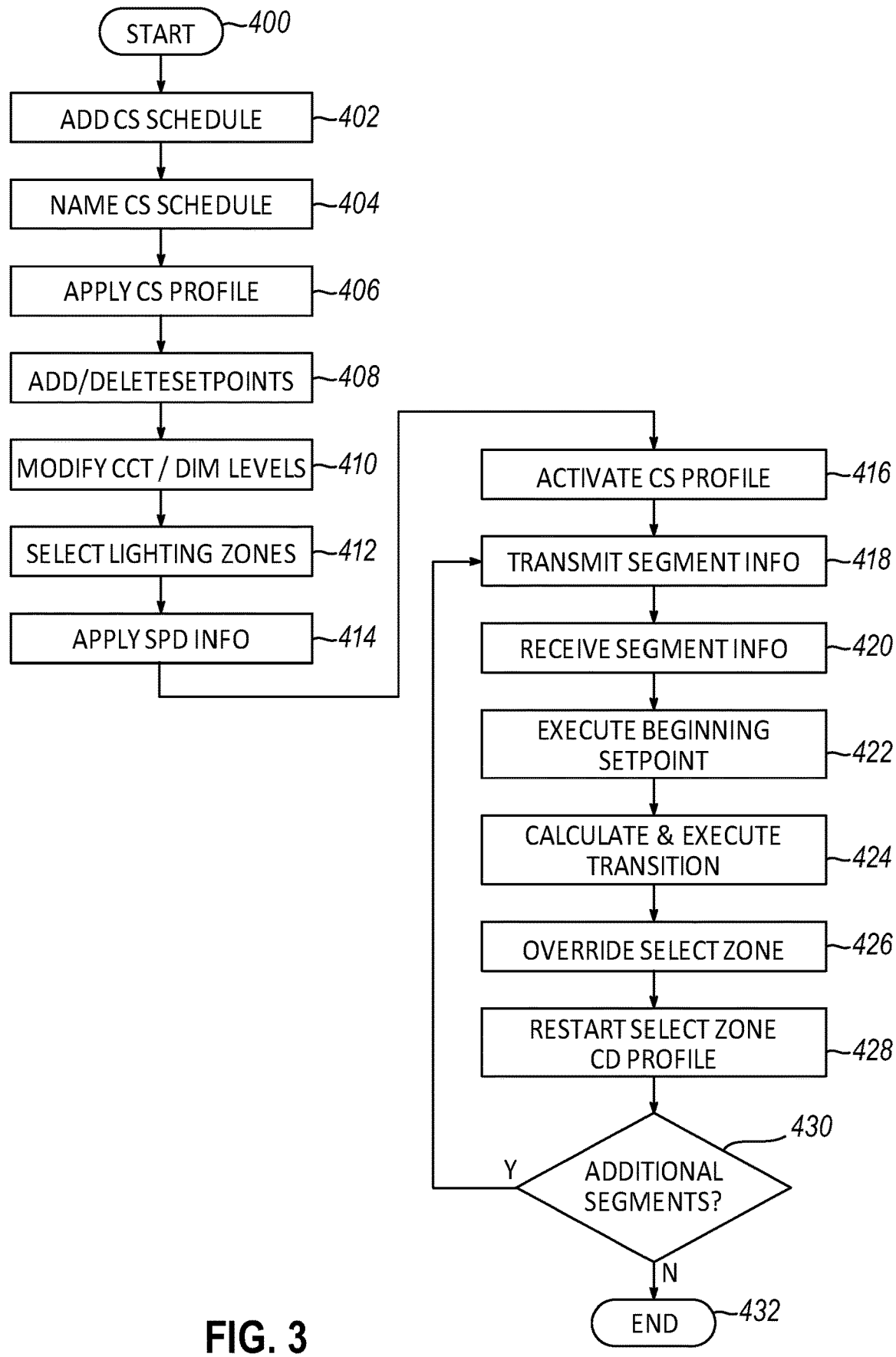
FIG. 3 illustrates an exemplary flowchart of circadian stimulus control for the first exemplary illumination control system.

The first exemplary illumination control system 10 described above and properly enabled advantageously can be used to provide circadian stimulus (CS) illumination control. Referring to FIGS. 3 and 4, an illustrative process 400 and graphic user interface (GUI) display layout 60 are shown.

The process 400 provides circadian stimulus illumination profiles that can be selected, modified, and applied to one or more lighting zones of one or more installations site systems 14. For example, as shown in Table 1 below, a CS profile schedule generally starts a period of time, for example, a 24 hour schedule, with a warm Correlated Color Temperature (CCT) and dim light level, transitions to a cool CCT and bright light level, and then finishes the day returning to a warm CCT and dim light level. For example, example preset circadian stimulus profile schedules shown in Table 1 below include "Nature," which can use and dynamically adjust for daily local sunrise, solar noon, and sunset time. The profile schedule starts with a CS level of 0.1, which is generally rest inducing, provided by a CCT level of 2700° Kelvin (K) and a dim level of 10%, then proceeds at sunrise to a CS level of 0.4 by increasing the dim level to 100%, advance to a CS level of 0.3 with a cooler CCT of 6500K and 100% dim level at solar noon, and at sunset returns to a rest inducing circadian stimulus level of 0.1 provided by a CCT of 2700K and a dim level of 10%. Advantageously, the transitions between these specific setpoints can be smooth linear or curvilinear transitions that include small, humanly imperceptible incremental changes over time. The transition of the CCT and dim level may be the same or different between setpoints depending on the capabilities of the lighting device and/or preferences.

Other preset CS profile schedules can be based on the time of day, a work day, or other preferred parameter, and can be applied to achieve other effects in addition or instead of CS, including profiles desired based on the location requirements, mood, safety, or other preferences, for example as provided in the profile names, descriptions, and CCT, dim, and CS levels provided in the example presets of Table 1:

TABLE 1

Example Preset Circadian Stimulus Profile Schedules

| Preset CS Profile | Description | | 5AM | 6AM | 12PM | 3PM | 6PM |
| --- | --- | --- | --- | --- | --- | --- | --- |
| Well | Default using equator sunrise sunset and average levels | CCT | 2700 | 4500 | 6500 | 4500 | 2700 |
| | | Dim | 10% | 100% | 50% | 30% | 10% |
| | | CS | 0.1 | 0.4 | 0.3 | 0.2 | 0.1 |
| Work | Increased levels throughout day - non-sleep inducing. | CCT | 3500 | 4500 | 6500 | 4500 | 3500 |
| | | Dim | 100% | 100% | 100% | 60% | 100% |
| | | CS | 0.29 | 0.4 | 0.5 | 0.29 | 0.29 |
| Calm | Decreased levels throughout the day | CCT | 2700 | 4500 | 4500 | 3500 | 2700 |
| | | Dim | 10% | 100% | 50% | 50% | 10% |
| | | CS | 0.1 | 0.4 | 0.26 | 0.17 | 0.1 |
| Learn | Slightly lower levels targeted at education | CCT | | 4500 | 4000 | 3500 | 3500 |
| | | Dim | | 100% | 70% | 50% | 100% |
| | | CS | | 0.4 | 0.28 | 0.17 | 0.29 |
| Cool | Maintain cooler temperatures throughout the day. | CCT | 4000 | 4500 | 6500 | | 4000 |
| | | Dim | 50% | 100% | 70% | | 50% |
| | | CS | 0.22 | 0.4 | 0.39 | | 0.22 |
| Warm | Maintain warmer temperatures throughout the day. | CCT | 2700 | 3000 | 3500 | | 2700 |
| | | Dim | 50% | 100% | 100% | | 50% |
| | | CS | 0.24 | 0.41 | 0.29 | | 0.24 |

TABLE 1-continued

Example Preset Circadian Stimulus Profile Schedules

| | | | −1 Hr Sunrise | Sunrise | Solar Noon | | Sunset |
|---|---|---|---|---|---|---|---|
| Nature | Uses local sunrise sunset instead of time | CCT Dim CS | 2700 10% 0.1 | 2700 100% 0.4 | 6500 100% 0.3 | | 2700 10% 0.1 |

Selecting the desired CCT and dim level can be based on preferred CS, CCT and/or brightness levels, and the capabilities of a lighting device, including the Spectral Power Distribution (SPD), range and/or subsets of CCT, and dimming capability. For example, in an environment in which maintaining a minimum level of lighting for safety may be required, some desired changes in CS throughout a profile may need to be based on a greater change in the CCT than would be required in environments suitable for allowing a full range of dimming. The specific combination of dimming level and CCT can be obtained, for example, from a lookup table correlating the parameters, an example of which is shown in Table 2:

TABLE 2

Example Circadian Stimulus Correlated with Dim Level and CCT

| | | Circadian Stimulus (CS) | | | | | | | |
|---|---|---|---|---|---|---|---|---|---|
| Dim Level | Lux | 2700K | 3000K | 3500K | 4000K | 4500K | 5000K | 5700K | 6500K |
| 0 | 0 | 0 | 0 | 0 | 0 | 0 | 0 | 0 | 0 |
| 10 | 50 | 0.058 | 0.071 | 0.034 | 0.049 | 0.061 | 0.071 | 0.083 | 0.086 |
| 20 | 100 | 0.113 | 0.137 | 0.07 | 0.097 | 0.119 | 0.137 | 0.158 | 0.162 |
| 30 | 150 | 0.162 | 0.193 | 0.104 | 0.142 | 0.171 | 0.194 | 0.22 | 0.225 |
| 40 | 200 | 0.205 | 0.24 | 0.136 | 0.182 | 0.216 | 0.242 | 0.271 | 0.276 |
| 50 | 250 | 0.242 | 0.28 | 0.166 | 0.217 | 0.255 | 0.283 | 0.313 | 0.319 |
| 60 | 300 | 0.275 | 0.314 | 0.193 | 0.249 | 0.289 | 0.318 | 0.349 | 0.355 |
| 70 | 350 | 0.304 | 0.344 | 0.219 | 0.278 | 0.319 | 0.349 | 0.38 | 0.386 |
| 80 | 400 | 0.329 | 0.37 | 0.242 | 0.304 | 0.345 | 0.375 | 0.406 | 0.412 |
| 90 | 450 | 0.352 | 0.392 | 0.264 | 0.327 | 0.369 | 0.399 | 0.428 | 0.434 |
| 100 | 500 | 0.372 | 0.412 | 0.285 | 0.348 | 0.39 | 0.419 | 0.448 | 0.454 |

Similarly, a lookup table with reduced complexity can be used if only a few CS levels are required for a CS profile schedule, an example of which is shown in Table 3:

TABLE 3

Example Select Circadian Stimulus Level Correlated to Dim Level by CCT

| CCT | .1 CS Dim Lvl | .3 CS Dim Lvl |
|---|---|---|
| 2700K | 10 | 70 |
| 3000K | 10 | 60 |
| 3500K | 20 | NA |
| 4000K | 20 | 80 |
| 4500K | 10 | 70 |
| 5000K | 10 | 60 |
| 5700K | 10 | 50 |
| 6500K | 10 | 50 |

Referring to FIG. 4, an exemplary GUI layout 60 for CS control of the illumination control system 10 is illustrated. The layout 60 includes an illustrated CS profile schedule 62. Each CS profile schedule 62 includes a series of segments 64 spanning a duration of time between a starting and ending setpoint 66a. Each setpoint 66a includes a time, a CCT level, and a dim level. The dim level is displayed along the X-axis, the time along the Y-axis, and the CCT is illustrated by a color or other shading or graphical gradient extending from the Y-axis upward to the selected dim level.

Setpoints 66a can be added to the selected CS profile schedule by touching the profile, for example, as indicated at new setpoint 66b. Setpoints 66a can be deleted or changed in time or dim level by touching an existing setpoint and dragging it along the X- or Y-axis, thereby changing the time and/or dim level, and by provide a popup setpoint display 68, which displays settings associated with the setpoint and provides a CCT adjustment slider.

One or more preset CS profile schedules 62 can be selected via a selectable popup preset listing 70, which can be elected after a touch selector 71 is touched to add a new CS profile schedule 62. A name can be assigned to each added schedule in selectable and editable field 72. The lighting zones (one or more lamps or lighting fixtures 40) to which a schedule is applied can be selected by slider 74 to be all compatible CS enabled zones at the installation site system 14, e.g., having CCT and/or dimming controls, or can be selectively apply by selecting zones to add or exclude from the listing at menu 78a. Additionally, lighting zones associated with more than one site system 14 can be assigned to a single CS profile schedule. Radio buttons 76 allow selection or deselection of display of the CCT and dim level, respectively, on the GUI 60. Existing CS profiles schedules can be selected for subsequent modification or activation from the listing at menu 78b.

Referring to FIG. 3, an illustrative flowchart of a process 400 for CS illumination control, for example, using illumination control system 10, is shown. The steps of the process may be executing, in part, by process associated with one or more of the remote server 12, gateway 24, and control devices 37. At step 402, a user can choose to add a CS profile schedule. At step 404, the CS profile schedule can be given a descriptive or otherwise identifying name. At step 406, a preset CS profile schedule, for example as shown in Table 1, can be selected, if desired. At step 408, the selected CS profile schedule can be modified by adding or deleting setpoints 66a, thereby adding or reducing the number of segments 64, if desired. At step 410, setpoints 66a can be modified to change the time, CCT, or dim level. At step 412, the default or selected lighting zones can be associated with the CS profile schedule. Advantageously, the GUI layout 60 or other GUI can be used to complete steps 402-412, for example, using a device 16 or 43 in communication with the remote server 18 and/or gateway 24 where the CS profile schedule can be stored.

At step 414, optionally, a processor associated with one of the remote server 12 or gateway 24 can take into account a specific SPD of a lighting device 40 associated with the CS profile schedule, in order to attain an optimize or preferred use of a combination of CCT and dimming to provide a desired CS level. At step 416, a single button can be selected to activate the CS profile schedule, for example the touch slider next to the schedule listing at menu 78b, or another mechanical or GUI or automation selection of the system 10. At step 418, the gateway 24 can transmit segment information to the lighting control devices 37 associated with the selected zones. For example, segment information can include the starting and ending setpoint data, including time, CCT, and dim levels, and CCT transition information between the starting CCT and ending CCT and dimming transition between the starting and ending dim levels. For example, transition information can reflect desire increments between the setpoints, or a desired or necessary linear or nonlinear transition depending on the capabilities of the lighting device 40.

At step 420, the control devices 37 receive the selected segment information and temporarily store the information necessary to complete the segment transition, i.e. until the segment is completed at the ending setpoint. By communicating CS profile schedule information only at the beginning of each segment 64, rather than throughout each segment, network communication traffic is minimized, and latency or other communication difficulties are reduced.

At step 422, the control devices 37 execute the beginning setpoint, setting the associate lighting device 40 to the desired CCT and dim level, thus providing the desired CS level. At step 424, the control devices 37 calculate and execute the incremental transitions between the starting and ending CCT and the starting and ending dim levels between the starting and ending times of the setpoints. Advantageously, the segment transitions can be small increments occurring periodically over a period of hours such that the transition from one increment to the next are imperceptible to humans.

At step 426, optionally, a select zone can be selected to override the present CCT and dim level, for example, by activating a manual switch 43 to turn a light fixture to full brightness to complete a work task, or to turn off a light fixture, for example, via an occupancy sensor 26. Advantageously, the control device 37 will continue receiving and determining the present CCT and dim level transitions, thereby at step 428 when the select zone override is restarted, the control device 37 can immediately return the associated lighting device 40 to the present CCT and dim level for the CS profile schedule. For example, upon subsequent actuation of the device used to override, or upon the end of a segment of the CS profile schedule, the override can cease and the CS profile schedule be followed by the associated zone and lighting devices 40. When a segment is complete or nearing completion, the gateway 24 will return to step 418 to execute the next segment if another is available, or the process will continue to step 432 at which it is completed.

Second Exemplary Circadian Stimulus Illumination System

Figure 5:
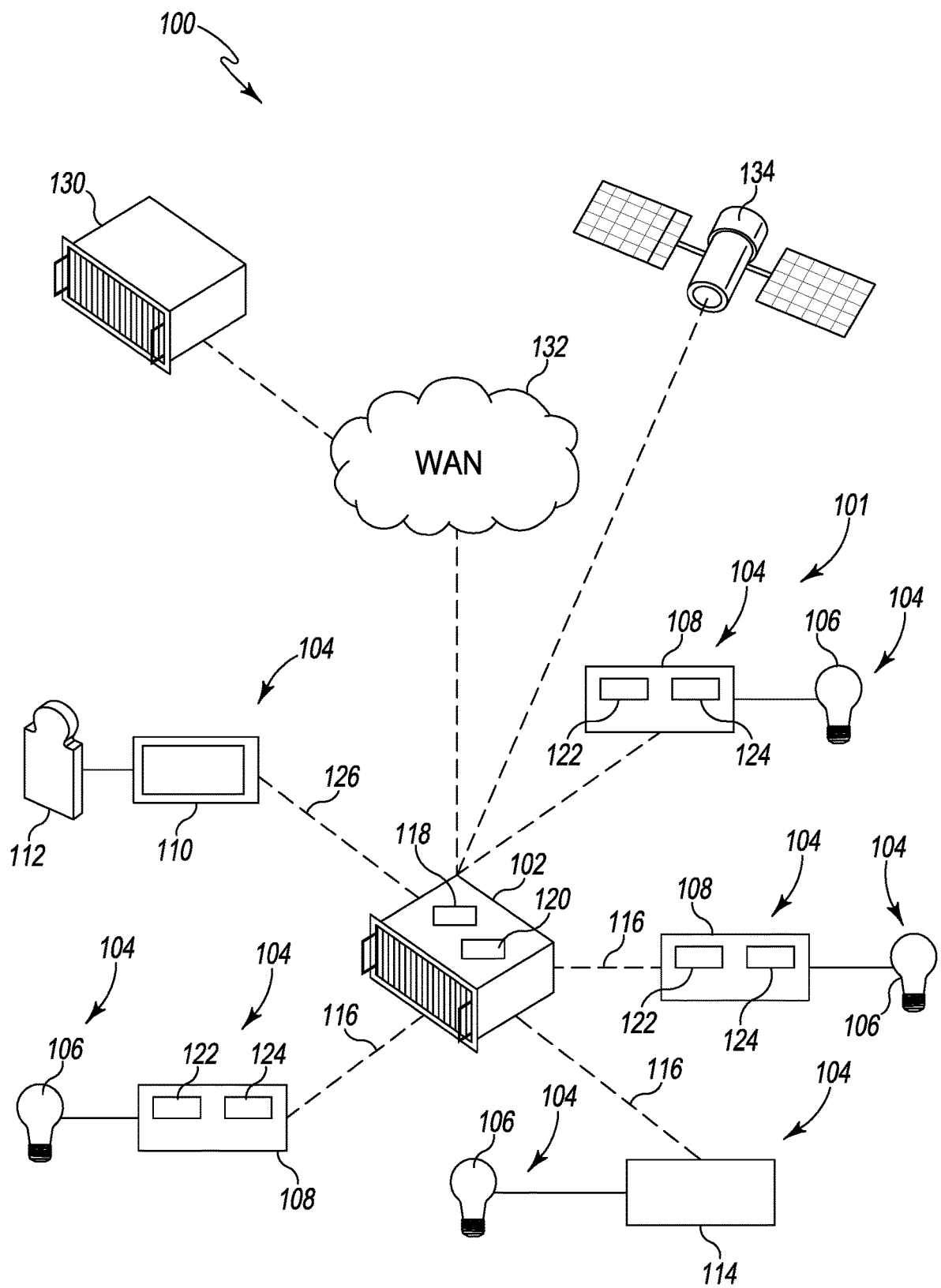
FIG. 5 illustrates a schematic block diagram of an second exemplary illumination control system, according to the present disclosure.

Depicted in FIG. 5 is an illumination control system 100 according to at least a second exemplary embodiment of the present disclosure. The second exemplary illumination control system 100 includes a local server 102 in connection with one or more site devices 104 located at a site system 101. Site devices 104 can include lighting devices 106 such as, for example, light emitting diode (LED) lamps, and lighting controllers 108 including, for example, an LED driver, associated with the lighting devices 106. As described herein, the local illumination control server 102 communicates lighting output adjustments to lighting controllers 108, wherein each lighting device 106 is coupled to and operated by a lighting controller 108. However, it should be understood that lighting controllers 108 may, in some embodiments, be integrated with one or more lighting devices 106.

Site devices 104 can also include various additional wired or wireless devices such as a user interface device 110 for a user 112 to connect to the local server 102, a daylight harvester 114 to provide ambient light sensor input to one or more lighting controllers 108 or the local server 102, or other known lighting and lighting-controlled devices such as occupancy sensors, touchscreens, and wall dimmers. The local server 102 communicates to site devices 104 via a wireless communication signal 116 of wireless communication link or network, for example, broad spectrum radio, Zigbee, microwave radio, WiFi, Bluetooth, or any other suitable local wireless communication means. In one exemplary embodiment, the wireless communication link is dedicated to be used only by a local server 102 to broadcast lighting control signals to the site devices 104 for affecting the color-temperature and/or dimming lighting output changes described herein. In an alternative embodiment, the wireless communication link is designated to be used similar to the local wireless network as used by the LIGHTCLOUD lighting control system available from RAB Lighting Inc., of Northvale, N.J., wherein a local server 102, a local gateway, and/or one or more site devices 104 utilize the network to transmit additional data throughout the local site 101 to and from the local server 102 and/or gateway such as, for example, lighting status indicators, power loss indicating signals, lighting scenes, etc.

The local server 102 facilitates wireless broadcasts of color temperature adjustment signals to one or more lighting devices 106, wherein the color temperature values can be calculated to mimic the color temperatures as provided by the sun in the local outdoor environment. In at least one embodiment, the one or more lighting controllers 108 within wireless communications range of the local server 102 can actively listen for, detect, and receive the broadcasted wireless communication signals 116 on a continuous or near-continuous basis, as is explained below, and adjust its lighting color temperature output according to the color temperature level provided by the broadcast signal 116. As such, the connected lighting devices 106 can output varying lighting effects or lighting patterns (for example, varying color-temperature effects, color-temperature schedules or patterns, and/or dimming effects) which remain in sync throughout the day, despite whether any individual lighting device is toggled on/off or the dim level is modified by a user.

In one embodiment the local server 102 broadcasts at a rate of about once per second, while refreshing the color-temperature broadcast signal 116 on a periodic basis which, in some examples, may be at the same rate as the local server 102 broadcasts or at faster or slower intervals. In an alternative embodiment the local server 102 broadcasts at a rate of about ten times per second. The lighting controllers 108 listen for broadcasted signals 116 on a periodic basis which may also mimic the rate of the local server 102, or at intervals which are faster or slower than the rate of the broadcasts. In one embodiment, lighting controllers 108 listen for broadcasted signals once every second. In an alternative embodiment, lighting controllers 108 listen for broadcasted signals ten times per second. As such, the system 100 is continuously revising the color-temperature output values such that the synchronized lighting patterns modify throughout the day wherein transitions between each lighting output affecting the pattern is imperceptible by the human eye.

To determine which color temperature to broadcast, the local server 102 can correlate operational information, that is, time and location data, with a schedule-to-color temperature conversion chart to calculate the appropriate color temperature of the sun. In alternative embodiments, the local server 102 can derive the appropriate color temperature using formulaic calculations, lookup tables, or through referencing internet sources. Site devices 104 in the system 100 then broadcasts a signal 116 containing a color-temperature value, or a data reference point for local lookup at the lighting controller 108 (for example, if the lighting controller 108 locally stored a reference data to color-temperature lookup table) to any and all lighting devices 106 which are within communication range and enabled to listen for and receive the broadcasted signal 116. Lighting devices within range can receive the broadcasted values and change their color temperatures to the received value.

Typically, outdoor atmospheric or ambient lighting conditions (i.e., color-temperatures) can be expressed as a unit of Kelvin. The kelvin range for ambient color-temperatures is about 1000K to 12000K, with the most common range for color-temperature lighting corrections being between about 2000K and 10000K, which generally correlates to ambient conditions as shown in Table 4 below:

TABLE 4

Example Color-Temperature and Ambient Condition Correlations

| Ambient Conditions | Approx. Color Temperature (Kelvin) |
|---|---|
| Clear Sky | 10000 K |
| Shade, Clear Day | 8000 K |
| Cloudy Sky | 6500 K |
| Noon Sunlight | 5300 K |
| Two Hours After Sunrise | 4500 K |
| One Hour After Sunrise | 3500 K |
| Sunrise/Sunset | 2000 K |

It should be appreciated, however, that any number of variable color-temperature steps may be interpolated from this data set. For example, the correlation data of server 102 may have a range of about 2000K-12000K but may include a multitude of intermediate steps within that range, for example, 2000K, 2005K, 2010K, . . . , 11090K, 11095K, 12000K. As such, the system 100 is capable of continuously updating the broadcasted signal 116 based upon the operational information of the server 102 to ensure the color-temperatures of all lighting devices 106 remain in sync and transitioning between color-temperature levels which appear natural and imperceptible by a human eye. In some embodiments, the lighting controller 108 adjusts lighting control based upon the capabilities and restrictions of the particular coupled lighting device 106. For instance, if a particular lighting device 106 is only capable to output color-temperatures between a smaller kelvin range than is being broadcast by the local server 102, the lighting controller 108 will recognize this and adjust the output driving signal sent to the lighting device 106.

Further, each lighting device can actively listen for a broadcasted signal 116 from the server immediately upon powering on, for example, as part of its start-up routine, and adjust its color-temperature output either before first illuminating, soon thereafter, or otherwise at an interval in which the color-temperature change or illumination output delay would be imperceptible by a human eye. Active listening includes enabling a radio module and permitting a receiver 122 to continuously listen for signals 116 broadcast over one or more frequencies. By doing so, this allows virtually any amount of lighting devices 106 to remain at the same color-temperature level throughout the day even if toggled on and off periodically, provided the lighting devices are within communication range of the broadcasted signal 116. In an exemplary embodiment, the receiver 122 continuously listens on one particular designated or previously-utilized frequency set by a user or by the local server 102. In alternative embodiments, the receiver 122 continuously listens across a particular range of frequencies or continuously listens using a frequency-hopping technique.

In some embodiments, the local server 102 also correlates the operational information with local daylight information to generate dim level (e.g., brightness) data to send via the broadcasted signal 116. The dim level data may correlate with the time of day (morning, afternoon, nighttime, or any period in between) to mimic the brightness of the local outdoor environment, or the dim level data may be controlled or modified by user input. In addition to ambient color-temperatures, brightness is also a factor in the circadian stimulus or response of humans, plants, and/or animals.

The illumination control system 100 may additionally include a user interface device 110 including, for example, a touchscreen control device, such as a smartphone or tablet computing device, having a user interface application or software installed directly thereon, interfacing with the local server 102 for configuring, monitoring and/or controlling the illumination control system 100. The user interface device 110 can connect to the local server 102 through a local wireless connection 126, e.g., WiFi, and can be used to set or adjust the operational information, adjust the color-temperature timing and/or broadcasting schedule, to develop or program a particular lighting pattern, or to directly control the color temperature values or brightness levels (e.g., dimming, ON/OFF, etc.) to broadcast via the communication signal 116.

Another exemplary site device 104 is a daylight harvester 114. The system 100 can optionally be configured to dim or switch lighting devices 106 in response to environmental light level as measured by the daylight harvester 114. More specifically, the daylight harvester 114 can be operated using open-loop control and it reacts to different sunlight levels, e.g., in a first mode the lights are illuminated and extinguished when the light sensor detects ambient light above/below a predetermined level. In another open-loop control mode, multiple thresholds are set and the lights are illuminated, dimmed, and extinguished depending on the ambient light sensed relative to the various thresholds. The daylight harvester 114 can also be used to detect environmental color temperature levels in real-time and communicate the levels to the local server 102 such that the local server 102 may use the daylight harvester 114 data in place of the operational information. For example, if operational information is not known, the daylight harvester 114 can be employed to detect and transmit the real-time color temperature values to the local server 102 for the local server 102 to process and broadcast via wireless communication 116 to the site devices 104 as per the normal operating procedure.

In some embodiments, the local server 102 includes additional functionality similar to other lighting control servers or may be, for example, a LIGHTCLOUD lighting control gateway made by RAB Lighting Inc. with added features for color-temperature adjustment. The remote server 130 may be remote from the site devices 104 and the local server 102. For example, Digi® Device Cloud, offered by Digi® International, Inc., is a public cloud platform for device network management that may be used for all or portions of the remote server 130. The remote server 130 may communicate with the local server 102 and the site devices 104 over a wide area network (WAN) 132, such as the internet or a cellular network, via a local area network (LAN), or via satellite 134. Cellular communication may be quicker to set-up, more secure and/or more reliable than other available communications means, such as an installation site's broadband internet connection. By using a cellular network, embodiments of the present disclosure are able to keep out of the organization's corporate network, which can assist in mitigating accidental creation of back doors through firewalls and into the user's corporate network that could potentially be used to create a security breach in the organization's corporate network.

Figure 6:
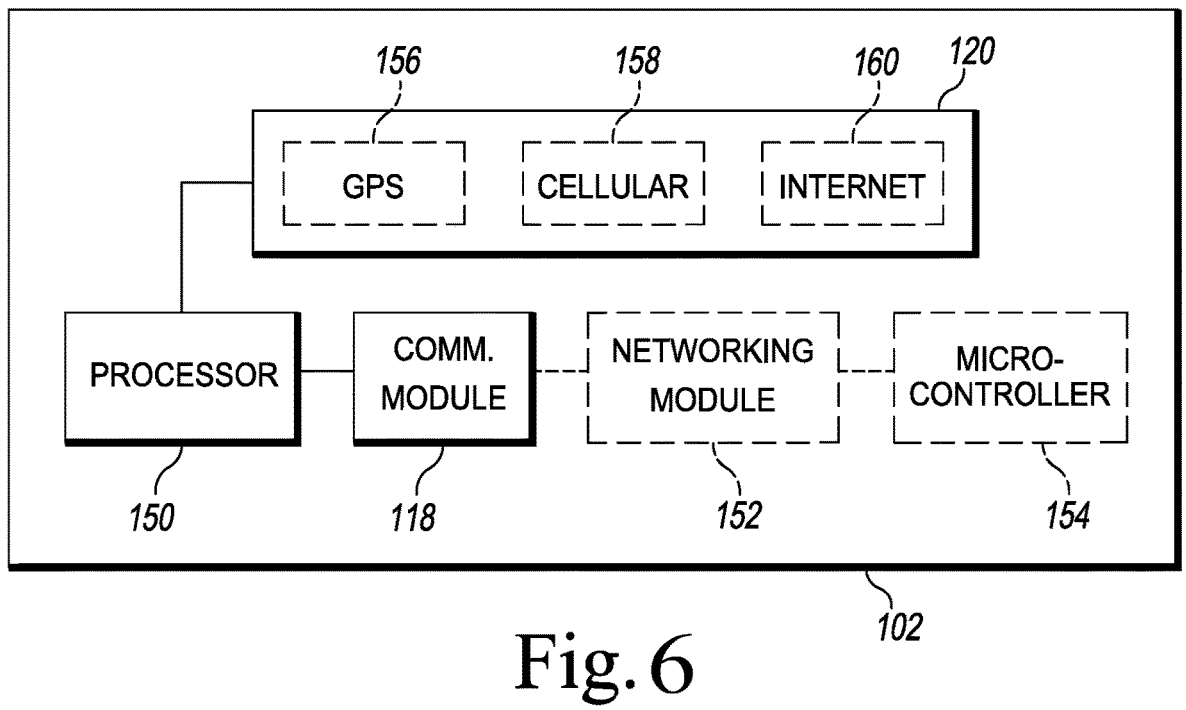
FIG. 6 illustrates a block diagram of an exemplary illumination control server of the illumination control system of FIG. 5.

Depicted in FIG. 6, the local server 102 may include particular computer components, including a processor, memory, storage, display, network interface, and input/output device configured and adapted for one or more of determining local daylight information, accepting user input, and broadcasting color-temperature values. The processor 150, or processors, may execute unique sets of instructions which may be implemented as computer readable program code and stored in memory or storage such that the local server 102 is configured as a special purpose system. In particular, hardware, software, and particular sets of instructions may transform the local server 102, or portions thereof, into a lighting control server, as described herein.

In one embodiment, the local server 102 includes a combination of computer hardware and software which facilitates communication with the site devices 104 of the illumination control system 100 and performance of the functions described herein such as, for example, a communications module 118 to broadcast the wireless communication signal 116, a networking module 152, and/or a microcontroller or processor 154. The communications module 118 can be configured to broadcast the wireless communication signal 116 on a repetitive basis, e.g., about ten times per second.

The communications module 118 of the local server 102 may be any known module which is capable of transmitting data wirelessly, for example, a LoRa Ra-01 433 MHZ Long-Range Wireless Transceiver Module by AI-Thinker or Mini RF Wireless Transmitter Module H34A-433 433 MHz Wireless Module by ICHSTAR. Further, any known and suitable networking modules and microcontrollers may be included in the server such as, for example, an ESP8266 ESP-01 WiFi Wireless Transceiver Module by Addicore or an ATmega328 8-bit AVR RISC-based microcontroller by MicroChip. In some embodiments, the local server 102 does not include wireless receiving capabilities.

The local server 102 further includes an operations module 120 that determines or receives operational information related to an amount and/or quality of light to be emitted from a lighting fixture, e.g., one or more of local daylight conditions, time, time zone, declination of the sun, altitude, date, geographical latitude and geographical longitude of the local server 102, desired daylight conditions (e.g., daylight conditions offset from local daylight conditions, specified light intensities, and/or specified color temperatures), or a desired lighting pattern received from a remote server, the operational information of which can include specified light intensities and/or color temperatures such that the desired light intensity and/or color temperature can be determined. The operations module 120 can include any suitable means for obtaining the operational information of the local server 102 such as by including one or more of a GPS module 156 (for example, a BU-353-S4 GPS receiver from US Globalsat Inc.), a cellular GSM module 158 (for example, a SIM800L GSM module from SIMCom), a WWVB radio controlled clock, an atomic clock, FM radio, a wired or wireless internet connection module 160, a user input module, a connection to a remote server directly or through a local gateway, and/or a direct connection to a local sensor.

Using one method, this calculation can be completed by referencing a default lookup table, database, or conversion chart which is stored onboard the local server 102. The lookup table can include color temperature values corresponding to particular intervals, e.g., every 15 minutes, throughout the day. Further, the lookup table, database, or conversion chart can be dynamic and update its values on a daily or weekly basis to provide better color temperature estimates as the seasons change for the local environment. Using another method, the color temperature calculation can be completed by referencing a lookup table or database which is stored external to the local server 102, e.g., on a remote server accessed through a connection to the internet. Using still another method, the default color temperature reference can be programmed and modified by a user 112 by adjusting controls either located directly on the device or via the user interface device 110.

As also should be appreciated by those skilled in the art, the exemplary illumination control system 100 can include more than one local server 102, wherein each local server 102 may function independently or function as a repeater to extend the broadcast range of another local server 102. Accordingly, each local server 102, in a first example, operates independently with regard to one another and broadcast lighting control signals each to a separate grouping of lighting controllers 108. For instance, each lighting controller 108 may individually store local server 102 pairing data indicative of which local server 102 it previously connected to, therefore all future broadcasts from that particular local server 102 will be received while broadcasts from a different local server 102 will be ignored. In this example, each lighting controller 108 will continue selectively listening to signals 116 from the same local server 102 unless or until the pairing is reset. The lighting controller 108 may include with each broadcasted signal 116 a unique device identifier identifying the local server 102 thereby allowing lighting controllers 108 to correctly pair in the event multiple local servers 102 are broadcasting within range of a lighting controller 108. In an alternative method of selectively listening to signals from a particular local server 102, each local server 102 may broadcast at a different frequency and therefore each lighting controller 108 may be configured to listen for a particular frequency.

To pair a lighting controller 108 to a particular local server 102, the lighting controller 108 is initially powered-on, wherein it listens for broadcasted signals from local servers 102. To ensure the correct local server 102 is "paired" to the lighting controller 108, all other local server 102 broadcasts are interrupted or are powered-down during this process. When a subsequent lighting controller 108 is ready to be initially powered-on for pairing, the intended local server 102 for pairing is solely powered-on and broadcasting while all other local servers 102 are not broadcasting. Once paired with a local server 102, the lighting controller 108 stores data indicative of the pairing and remembers which local server 102 to listen for during operation.

In a second example, multiple local server 102 pair with each other via a wireless network connection, for example, within a mesh network. In this example, each local server 102 operates dependently and therefore only a single local server 102 is required to obtain operational information to share with the other local servers 102.

Figure 7:
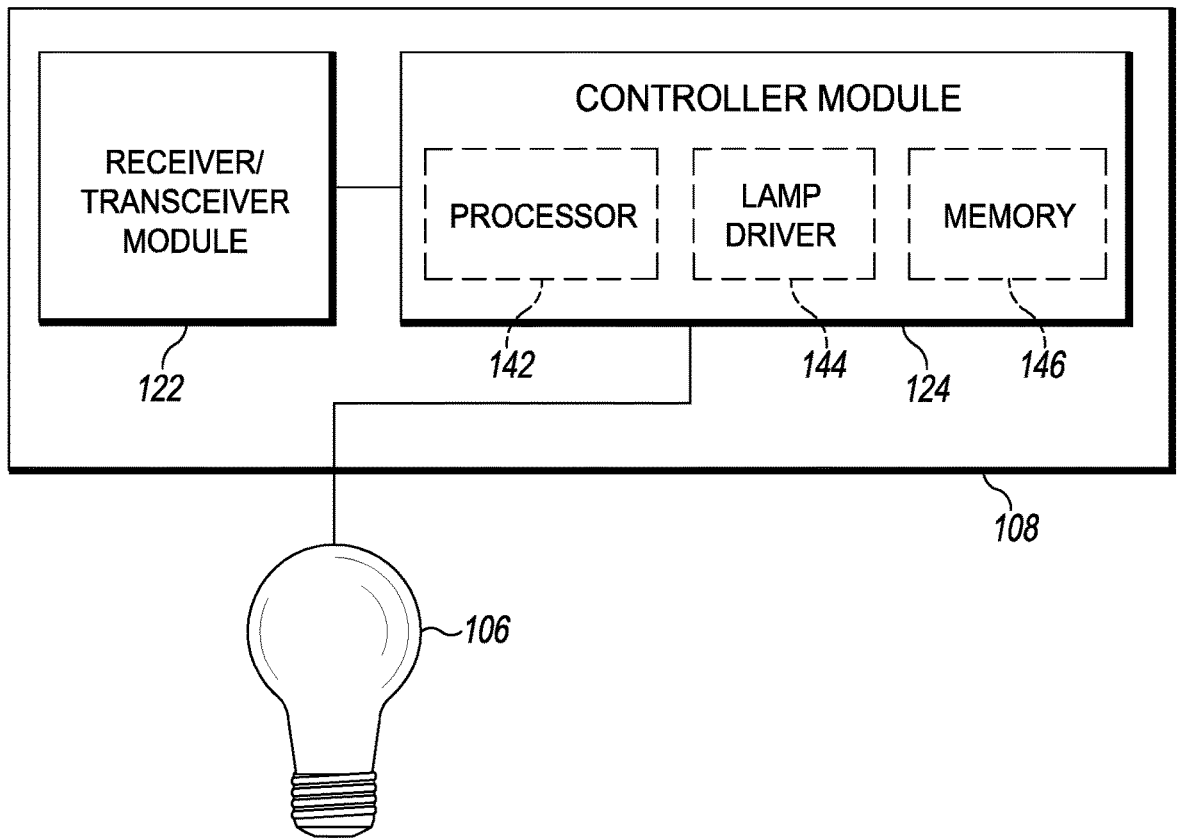
FIG. 7 illustrates a block diagram of an exemplary lighting control device of the illumination control system of FIG. 5.

Depicted in FIG. 7, an exemplary lighting controller 108 can function as a wireless receiver or transceiver and can provide color temperature adjustment controls to one or more associated lighting devices 106, dimming, and/or ON/OFF control for lighting devices 106 on a common electrical circuit. The color temperature adjustment, dimming, or ON/OFF commands may be received by the wireless communication signal 116 broadcasted from the local server 102. To facilitate communication with the local server 102 and control of the lighting devices 106, a lighting controller 108 can include a receiver module 122, having one of a wireless receiver and/or transceiver, and a controller module 124, having one or more of a processor 142 and a microcontroller, a lighting driver (e.g., an LED driver) 144, and/or a memory module 146. The receiver module 122 can be, for example, a LoRa Ra-01 433 MHZ Long-Range Wireless Transceiver Module by AI-Thinker or an LR45A Receiver Module by ICHSTAR. Further, the controller module 124 can be, for example, an ATmega328 8-bit AVR RISC-based microcontroller by MicroChip. In some embodiments, the lighting controller 108 associated with one or more lighting devices 106 does not include wireless transmitting capabilities.

The exemplary lighting controller 108 may include additional functionality similar to other lighting controllers or may be, for example, a LIGHTCLOUD lighting controller available from RAB Lighting Inc. of Northvale, N.J., which may in some instances include a transceiver and serve as a repeater within a mesh network, and including features for color-temperature adjustment. Lighting controllers 108 may be installed at a junction box, in a breaker box or lighting panel, or integral with a lighting device 106 (e.g. affixed to the lamp or light fixture housing). Further, lighting controllers may form a wired or wireless connection with the lighting devices 106.

An exemplary lighting device 106 may be a simple lamp such as, for example, an LED array or incandescent bulb, or may be a more complex lighting device such as a panel housing an array of LEDs, for example, a WS2812B Intelligent Control LED Integrated Light Source by WorldSemi. The lighting device 106 may house within it all or some of the components of the lighting controller 108 to communicate with the local server 102. The lighting device 106 can be capable of receiving a control signal from the local server 102 or lighting controller 108 which consists of a color temperature value or illumination setting and altering its lighting state according to the control signal. To accomplish an illumination output of varying color temperature values, the exemplary lighting device 106 can consist of one or more tunable LEDs capable of varying their output ratings as measured in degrees of kelvin (K) or can consist of LEDs capable of selectively illuminating in combinations to generate a particular output. Further, one may select an optical component, such as a lens or filter to illuminate at the desired color temperature. Generally, a lower kelvin output means the light appears more yellow while a higher kelvin output means the light appears whiter or bluer. For example, CFLs and LEDs are typically made to match the color of incandescent light bulbs at around 2700-3000 K. Whiter light is typically output at 3500-4100 K while bluer light is output at around 5000-6500 K. The illuminated color temperature of the exemplary embodiment can be selected from known ranges, for example, 2200-6000 K.

Figure 8:
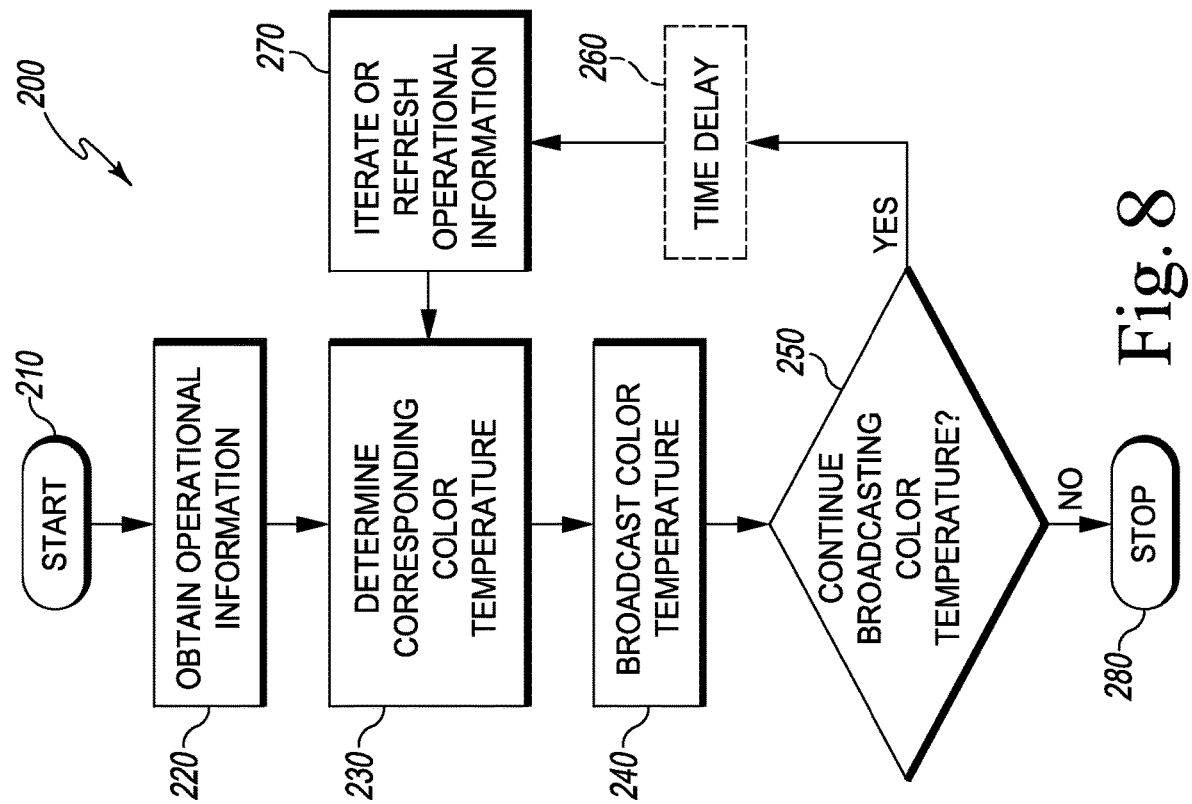
FIG. 8 is a flowchart representing an exemplary method of providing lighting adjustments to one or more site devices of the illumination control system of FIG. 5.

Depicted in FIG. 8 is a flowchart representing an exemplary method 200 of providing lighting adjustment output signals by the local server 102 to one or more site devices 104 of the illumination control system 100. The method begins at a START, Step 210, which generally refers to the powering on of the local server 102 and all of its components and circuitry, and proceeds to a first step, shown at Step 220, in which the local server 102 obtains operational information.

Once the local server 102 obtains the operational information, the local server 102 can then correlate the data at Step 230 with an environmental lighting pattern affecting biological circadian rhythms (e.g. in humans, plants and/or animals). The lighting pattern, for example, may include varying color temperature, hue, and/or brightness levels corresponding to typical daylight illumination changes within the local outdoor environment throughout the 24-hour day cycle.

At Step 240, the local server 102 wirelessly broadcasts communication signals 116, via the communications module 118, containing the desired color temperature value to be output by the lighting devices 106 within communication range of the signals 116. The exemplary communications module 118 can be a low-frequency radio which is capable of broadcasting output signals greater distances with fewer obstructions, although other devices can be used as appreciated by one skilled in the art. Further, a low-frequency radio does not require large bandwidth for normal operation. Site devices 104, such a lighting controllers 108 and lighting devices 106, can be capable of receiving the broadcast signals and changing their lighting outputs accordingly.

At Step 250, the local server 102 will determine whether it should continue broadcasting the current color temperature output values. In one instance, the local server 102 may determine it should not continue broadcasting because the local server 102 has been powered down or a user 112 has directed it to cease and in that case the method proceeds to STOP at Step 280. Otherwise, the local server 102 will generally continue broadcasting and proceed to Step 260.

At Step 260, the local server 102 can optionally apply a time delay to lengthen the amount of time between the broadcasts from the local server 102 to the site devices 104. In an exemplary embodiment, the local server 102 broadcasts communication signals 116 at or near ten times per second, although one can appreciate that this rate can be shortened or lengthened as needed. Therefore, depending on the inherent processing speed and time delays produced by the local server 102 and its associated components, a time delay can be introduced if necessary to slow the rate of the output broadcast signal. The time delay can be chosen at any desired interval preferred by a user. In the exemplary embodiment, a time delay of a particularly short length of time is chosen to ensure lighting controllers 108 first joining the network or listening for broadcasts receive a signal in a quick enough manner such that the connected lighting devices 106 first illuminate or change illuminations at rates of speed imperceptible by the human eye. For example, the chosen time delay can permit the local server 102 to broadcast at a rate of about 10 times per second.

Once the local server 102 is prepared to initiate a new color temperature lookup or conversion to broadcast, the local server 102 at Step 270 can refresh the operational information to ensure the correct output signal is calculated. This can preferably be done using the operations module 120 in the same way as in Step 220; however, if the connection to the operations module 120 has been lost or the data is otherwise unavailable, the local server 102 can simply iterate the time and/or date according to the last known data in conjunction with the known time delays since the last set of data was obtained or iterated. Once an updated set of data has been obtained or calculated, the process can again continue with Step 230 and determine the latest color temperature which corresponds to the operational information.

Figure 9:
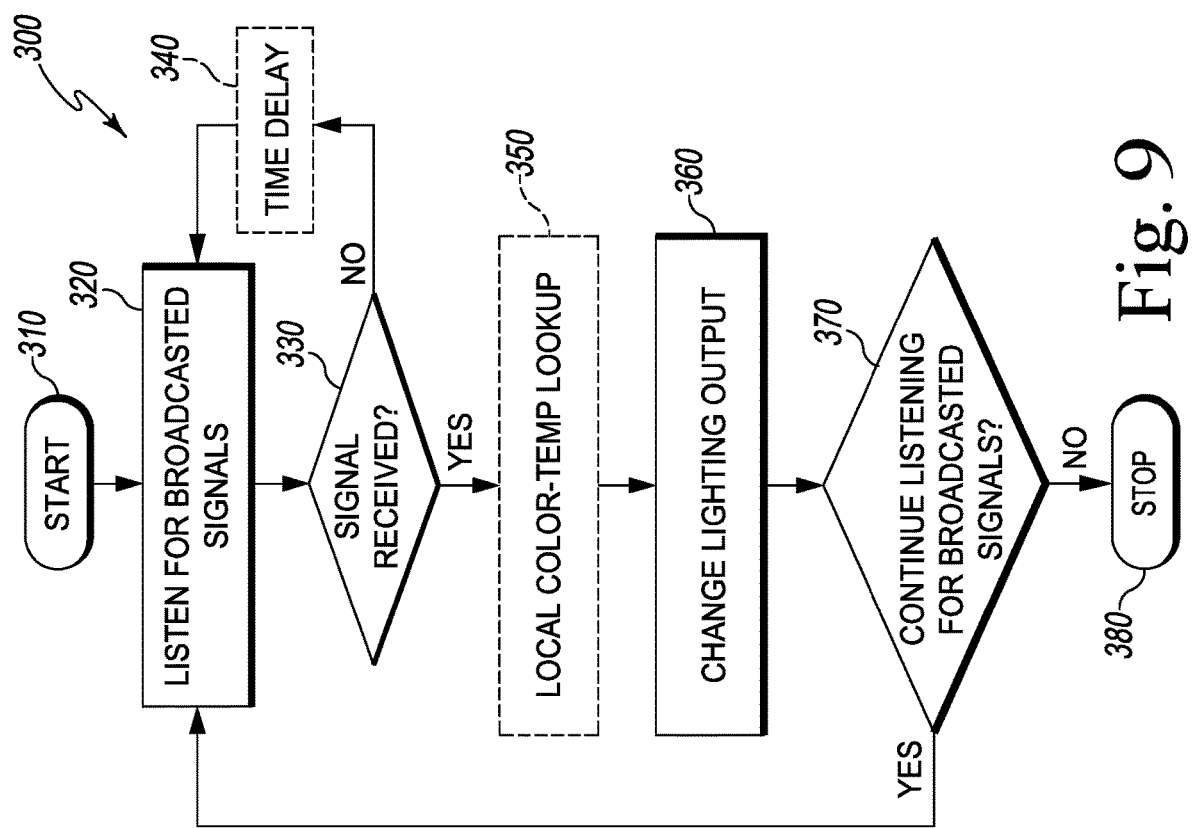
FIG. 9 is a flowchart representing an exemplary method of receiving lighting adjustments by one or more site devices of the illumination control system of FIG. 5.

Depicted in FIG. 9 is a flowchart representing an exemplary method 300 of receiving lighting adjustments by one or more site devices of the illumination control system 100. The method begins at a START, Step 310, which generally refers to the powering on of the local lighting control 108 and all of its components and circuitry, and proceeds to a first step, shown at Step 320, in which the lighting controller 108 listens for broadcasted signals from one or more local servers 102. If a pairing and received signal with a particular local server 102 has already been made in a prior instance, the lighting controller 108 will listen for a broadcast from that particular local server 102. If a pairing with a particular local server 102 has not already been made in a prior instance, the lighting controller 108 will listen for any broadcast from that same local server 102 as before. At Step 330, the lighting controller 108 will determine whether a signal was received as result of the active listening of Step 320. If a signal was not received, the method 300 moves to Step 340 wherein a time delay can optionally be introduced to slow the rate of processing. The time delay can be chosen at any desired interval preferred by a user. In the exemplary embodiment, a time delay of a particularly short length of time is chosen to ensure lighting controllers 108 first joining the network or listening for broadcasts listen for and receive a signal in a quick enough manner such that the connected lighting devices 106 first illuminate or change illuminations at rates of speed imperceptible by the human eye. For example, the chosen time delay can permit the lighting controller 108 to repetitively listen at a rate of about 10 times per second. The rate can be increased or decreases as desired.

If a signal is received at Step 330, the method 300 can optionally move to Step 350 wherein the lighting controller 108 receives a data packet for cross referencing with a locally-stored color-temperature lookup table or to otherwise input into a locally-stored formula to determine a color-temperature output value. In the exemplary embodiment, this step is performed at the local server 102 and the color-temperature is broadcast to lighting controllers 108. Therefore, in the exemplary embodiment, the method 300 moves from Step 330 to Step 360 wherein the lighting controller 108 processes the received signal and directs a change in the output of the connected lighting device 106 according to the received signal. At Step 370, the lighting controller 108 will in most cases return to Step 320 to continue listening for broadcasted signals for further updates to the lighting output. Otherwise, such as if the lighting controller 108 is powered-down or interrupted, the method will end at Step 380.

In at least one embodiment of the disclosure, site devices 104 (e.g. lighting controllers 108 and/or lighting devices 106) listen for the broadcasted communication signal 116 and adjust light output to synchronize with the color temperature value provided by the communication signal 116, and therefore one another, throughout the day. Listening can consist of enabling a radio module and permitting a receiver to listen for signals broadcast over a particular frequency range, or enabling a particular communications module to listen for compatible signals. Lighting controllers 108 and/or lighting devices 106 also listen for the broadcast immediately upon being powered on (such as during the device's start-up routine), so the lighting devices 106 can be periodically powered off and on without falling out of sync with the group. By doing so, the individual site devices 104 do not require equipment, such as atomic clocks or other commonly used equipment, which obtain or calculate operational information at the site device 104. Further, by continually and actively listening for communication signals 116 and updating lighting output nearly instantaneously, a user is virtually unable to detect any delays or lighting changes as the lighting device 106 powers on. Still further, since the local server 102 can broadcast a one-way low-frequency communication signal 116 in all directions, any number of site devices can listen (i.e., search) for and process the information contained in the signal 116. In the event a broadcasted communication signal 116 is not received by a lighting controller 108 and/or lighting device 106 immediately upon powering on, the lighting controller 108 and/or lighting device 106 can be pre-configured to adjust the light output to a particular color temperature, or alternatively, to the color temperature provided by the most recently received broadcasted communication signal 116 such as the last signal 116 received prior to the lighting controller 108 and/or lighting device 106 powering down.

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used in combination with some or all of the features of other embodiments as would be understood by one of ordinary skill in the art, whether or not explicitly described as such. One or more exemplary embodiments have been shown and described, and all changes and modifications that come within the spirit of the disclosure are desired to be protected.

For example, the preset and customizable circadian stimulus profile schedules disclosed with the first exemplary embodiment may be used with the second exemplary embodiment. No disclaimer of such combinations that are not explicitly disclosed is intended. It is contemplated that the various teachings herein may be arranged and applied in numerous other ways. It is also contemplated that some variations may omit certain features referred to in the examples. Therefore, none of the aspects or features referred to should be deemed critical unless otherwise explicitly indicated as such. It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A lighting control system for lighting devices for use with a graphical user interface including a processor and a touchscreen, comprising:
   a first lighting controller for installation at a first site, the lighting controller including:
      a wireless transceiver in wireless communication with the lighting devices located at the first site and for controlling the correlated color temperature (CCT) and dimming level of lighting devices located at the first site; and
      a memory storing a plurality of circadian stimulus (CS) profile schedules, each one of the plurality of CS profile schedules define preset, configurable segments spanning a duration of time between a beginning scheduled setpoint and an ending scheduled setpoint, each segment having a transition profile between the beginning and ending scheduled setpoint, and the beginning setpoints and ending scheduled setpoints each having a CCT, a dimming level, and a time, and the transition profile including CCT and dimming level information; and
   an application executed by the processor of the graphical user interface, the graphical user interface in communication with the lighting controller, the application enabling a user to use the touchscreen to:
      select one of the plurality of CS profile schedules;
      select one of the scheduled setpoints of the selected one of the plurality of CS profile schedules;
      modify independently one or more of the CCT, the dimming level, and the time for the selected one of the scheduled setpoints;
      select at least one lighting zone of the lighting devices; and
      apply the selected one of the plurality of CS profile schedules to the selected at least one lighting zone of lighting devices; and
   wherein the lighting controller transmits to the selected at least one lighting zone of the lighting devices the beginning scheduled setpoint, ending scheduled setpoint, and transition profile for each segment at a time for which execution of the immediately preceding segment by the at least one lighting one of lighting devices is complete or nearing completion.

2. The lighting control system of claim 1, wherein the application further enables the user to use the touchscreen to add and delete scheduled setpoints to the selected one of the plurality of CS profile schedules.

3. The lighting control system of claim 1, wherein the lighting controller detects a subset of the plurality of lighting devices responsive to controlling the CCT and dimming level, and wherein selecting one of the plurality of CS profiles schedules automatically assigns to it the subset of the plurality of lighting devices.

4. The lighting control system of claim 1, further comprising a switching device to control at least a subset of the selected at least one lighting zone of lighting devices, and wherein activating the switching device overrides the selected one of the plurality of CS profile schedules with one of a CCT and dimming level selected by the switching device.

5. The lighting control system of claim 4, wherein a lighting device turned off by the switching device continues to receive the beginning scheduled setpoint, ending scheduled setpoint, and transition profile for each segment, thereby enabling the lighting device turned on by the switching device to immediately operate in accordance with a current segment of the selected one of the plurality of CS profile schedules.

6. The lighting control system of claim 1, wherein the application further enables the user to use the touchscreen to add and remove lighting zones from a selected one of the plurality of CS profile schedules.

7. The lighting control device of claim 1, wherein the CCT and dimming level for each scheduled setpoint is determined based on at least a desired circadian stimuli level for the schedule setpoint time.

8. The lighting control device of claim 7, wherein the CCT and dimming level for each scheduled setpoint is further determined based on the spectral power distribution (SPD) of at least one of the lighting devices.

9. The lighting control device of claim 7, further comprising a remote server in communication with the lighting controller, and wherein the SPD of at least one of the lighting devices is received by the remote server and the CCT and dimming level for each scheduled setpoint is determined by the remote server.

10. The lighting control device of claim 1, further comprising a remote server in communication with the lighting controller, and wherein the plurality of CS profile schedules is stored on the remote server and the selected one of the CS profile schedules is stored on the lighting controller and spans at least 24 hours.

11. The lighting control device of claim 1, wherein the lighting controller stores CS profiles schedules spanning at least 7 days.

12. The lighting control device of claim 1, further comprising a remote server and a second lighting controller at a second site, and wherein:
   the remote server is in communication with the first and second lighting controllers; and
   the selected one of the plurality of CS profile schedules is stored and activated for the first and the second lighting controller.

13. The lighting control device of claim 1, wherein the application enables the graphical user interface to display a graphical representation of the selected one of the plurality of preset CS profile schedules, including an X-axis for time, Y-axis for dimming level, and shade for CCT.

14. The lighting control system of claim 1, wherein:
   a plurality of lighting zones each include a subset of the lighting devices; and
   the application further enables the user to select one of the plurality of CS profile schedules for each of the plurality of lighting zones using the graphical user interface; and
   thereby different ones of the plurality of lighting zones are simultaneously controlled according to different ones of the plurality of CS profile schedules.

15. A lighting control system for use with a graphical user interface including a processor and with a plurality of lighting devices each having a first wireless transceiver, comprising:
   a lighting controller including:
      a second wireless transceiver in communication with the first wireless transceivers and for controlling the CCT and dimming level of the plurality of lighting devices; and
      a memory for storing a plurality of preset circadian stimulus (CS) profile schedules, each one of the plurality of preset CS profile schedules define preset, configurable segments spanning a duration of time between a beginning scheduled setpoint and an ending scheduled setpoint, each segment having a transition profile between the beginning and ending scheduled setpoint, and the beginning setpoints and ending scheduled setpoints each having a CCT, a dimming level, and a time, and the transition profile including CCT and dimming level information; and an application executed by the processor of the graphical user interface, the graphical user interface in communication with the lighting controller, the application enabling a user to:

select one of the plurality of preset CS profile schedules;

select one of the scheduled setpoints of the selected one of the plurality of preset CS profile schedules;

modify independently at least one of the CCT, dimming level, and time for the selected one of the scheduled setpoints; and apply the selected one of the plurality of preset CS profile schedules to at least a subset of the plurality of lighting devices; and wherein the lighting controller transmits to the first wireless transceivers the beginning scheduled setpoint, ending scheduled setpoint, and transition profile for each segment at a time for which execution of the immediately preceding segment by the at least a subset of the plurality of lighting devices is complete or nearing completion.

16. The lighting control system of claim 15, wherein the application further enables a user to select the subset of the plurality of lighting devices using the graphical user interface.

17. The lighting control system of claim 15, wherein each lighting device includes a control device storing each segment, the control device capable of providing incremental changes in CCT and dimming level between each beginning scheduled setpoint and end scheduled setpoint in accordance with the transition profile.

18. The lighting control system of claim 17, wherein each lighting device further includes an integral wireless receiver, and an LED driver, the wireless receiver in communication with lighting controller, the wireless receiver in communication with the LED driver, and the LED driver responsive to CCT and dimming level control signals received from the lighting controller.

19. The lighting control system of claim 15, wherein the time for each scheduled setpoint is dynamically adjusted for local sunrise and sunset based on location data stored in the memory.

20. A lighting control system for use with a plurality of lighting devices each having a first wireless transceiver, comprising:

a lighting controller including:

a second wireless transceiver in communication with the first wireless transceivers and for controlling the correlated color temperature (CCT) and dimming level of the plurality of lighting devices; and a memory storing a plurality of circadian stimulus (CS) profile schedules, each of the plurality of CS profile schedules including preset, configurable segments spanning a duration of time between beginning and ending setpoints, each setpoint having a CCT, a dimming level, and a time, and each segment having a CCT transition profile and dimming level transition profile defined between each beginning and ending setpoint; and a graphical user interface in communication with the lighting controller, the graphical user interface including a processor and a touchscreen enabling a user to:

select one of the plurality of CS profile schedules;

select one of the setpoints of the selected one of the plurality of CS profile schedules;

modify independently one or more of the CCT, the dimming level, and the time for the selected one of the setpoints; and apply the selected one of the plurality of CS profile schedules to at least a subset of the plurality of lighting devices; and wherein;

the lighting controller transmits to the first wireless transceivers of the selected at least a subset of the plurality of lighting devices the beginning setpoint, ending setpoint, and the transition profiles for each segment at a time for which execution of the immediately preceding segment by the at least a subset of the plurality of lighting devices is complete or nearing completion.

* * * * *